(12) United States Patent
Dettori et al.

(10) Patent No.: US 11,921,039 B2
(45) Date of Patent: Mar. 5, 2024

(54) METHOD AND ACTIVE CONTROL SYSTEM FOR FOOD TREATMENT PROCESSES

(71) Applicant: BIOSABBEY S.R.L., Milan (IT)

(72) Inventors: Gianluca Dettori, Milan (IT); Raimondo Francesco Dettori, Milan (IT)

(73) Assignee: BIOSABBEY S.R.L., Milan (IT)

( * ) Notice: Subject to any disclaimer, the term of this patent is extended or adjusted under 35 U.S.C. 154(b) by 362 days.

(21) Appl. No.: 17/465,357

(22) Filed: Sep. 2, 2021

(65) Prior Publication Data
US 2022/0099569 A1 Mar. 31, 2022

(30) Foreign Application Priority Data

Sep. 4, 2020 (IT) .................. 102020000020989

(51) Int. Cl.
| | | |
|---|---|---|
| G01N 21/3563 | (2014.01) | |
| A01J 25/00 | (2006.01) | |
| A23B 4/02 | (2006.01) | |
| A23C 19/097 | (2006.01) | |
| G01N 21/359 | (2014.01) | |
| G01N 33/04 | (2006.01) | |
| (Continued) | | |

(52) U.S. Cl.
CPC .......... *G01N 21/3563* (2013.01); *A01J 25/00* (2013.01); *A23B 4/02* (2013.01); *A23C 19/0973* (2013.01); *G01N 21/359* (2013.01); *G01N 33/04* (2013.01); *G01N 33/12* (2013.01); *G05B 13/0265* (2013.01)

(58) Field of Classification Search
CPC ........ A01J 25/00; A23B 4/02; A23C 19/0973; G01N 2021/8416; G01N 21/35; G01N 21/3563; G01N 21/3577; G01N 21/359; G01N 2201/1296; G01N 33/02; G01N 33/04; G01N 33/12; G05B 13/0265; G05B 19/00; G05B 11/00
See application file for complete search history.

(56) References Cited

U.S. PATENT DOCUMENTS

| | | | | |
|---|---|---|---|---|
| 2004/0146615 | A1* | 7/2004 | McDonald | G01N 33/02 426/231 |
| 2009/0236333 | A1* | 9/2009 | Ben-Shmuel | H05B 6/6447 219/710 |

(Continued)

FOREIGN PATENT DOCUMENTS

WO 2010/025254 A1 3/2010

OTHER PUBLICATIONS

Marimin M et al., Intelligent System for Pasteurised Milk Quality Assessment and Prediction Marimin 1, Proceedings of the 51st Annual Meeting of the ISSS - 2007, Tokyo, Japan, Jul. 31, 2007.

(Continued)

*Primary Examiner* — Kidest Bahta
(74) *Attorney, Agent, or Firm* — Bay State IP, LLC

(57) ABSTRACT

A method and a control system of a food treating process made of a plurality of sub-processes is disclosed. The system comprises a plurality of product sensors including at least a spectrograph sensor and a thermograph sensor, plant sensors, control devices, a main hardware and software architecture apt, and a database structure to provide timely and automatic regulation controls, preferably exploiting synergies between various optimised parallel processes.

10 Claims, 7 Drawing Sheets system architecture

(51) Int. Cl.
    *G01N 33/12*     (2006.01)
    *G05B 13/02*     (2006.01)

(56) References Cited

U.S. PATENT DOCUMENTS

| | | |
|---|---|---|
| 2012/0269925 A1 | 10/2012 | Farotto |
| 2015/0299815 A1 | 10/2015 | Morishima |
| 2015/0366219 A1 | 12/2015 | Stork Genannt Wersborg |
| 2018/0085003 A1* | 3/2018 | Goldring ................ A61B 5/746 |

OTHER PUBLICATIONS

Christian Cimander et al., Sensor Fusion for On-Line Monitoring of Yoghurt Fermentation, Journal of Biotechnology, vol. 99, No. 3, Nov. 1, 2002, pp. 237-248, XP055338626, Issn: 0168-1656.
Italian Patent Office, Search Report, May 3, 2021.

* cited by examiner

Fig. 1 – system architecture

Fig. 2 – Logical diagram of the system

Fig. 3 – processing steps, dairy industry

Fig. 4 – processing steps, dairy industry

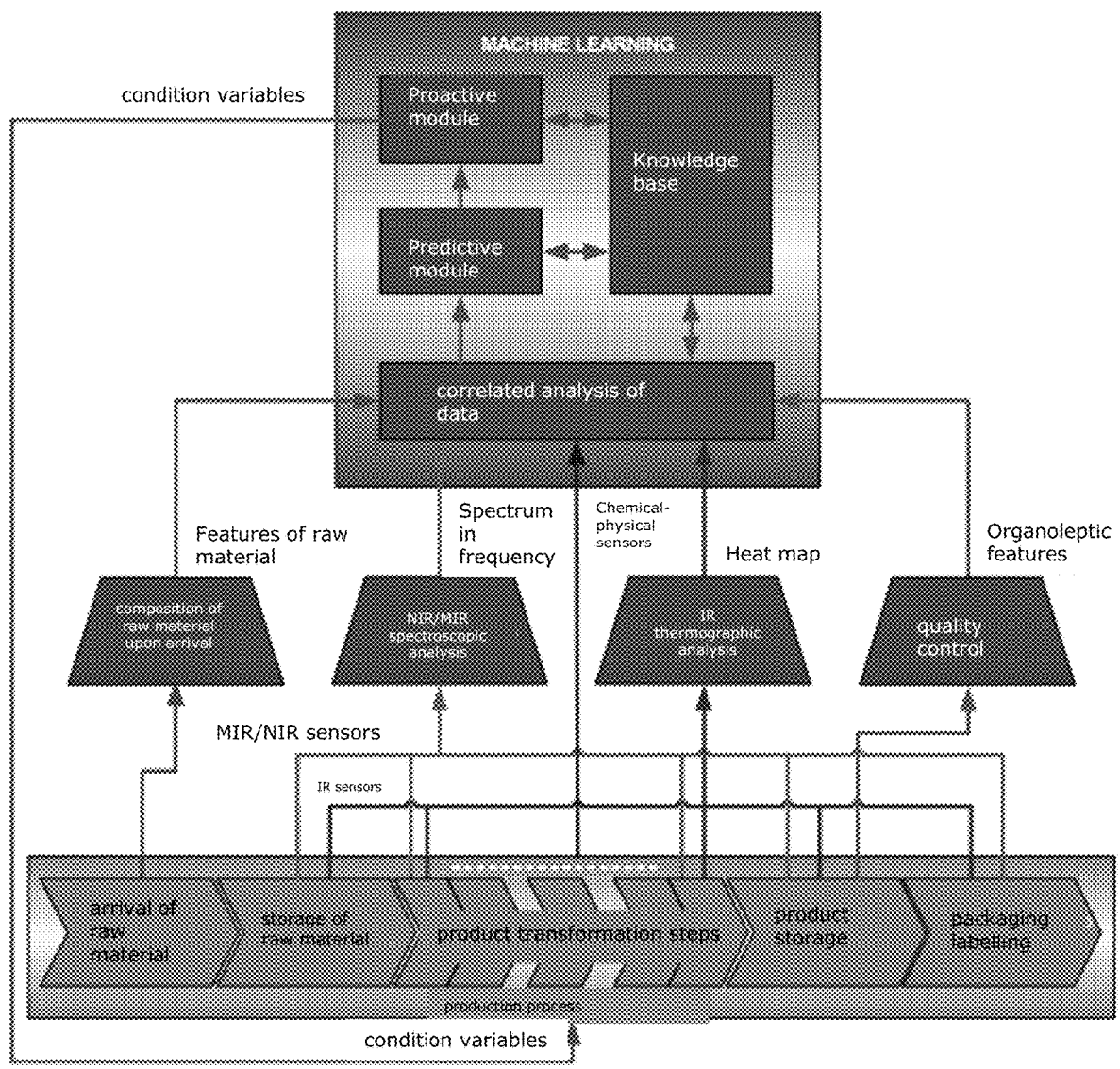
Fig. 6 – functional diagram

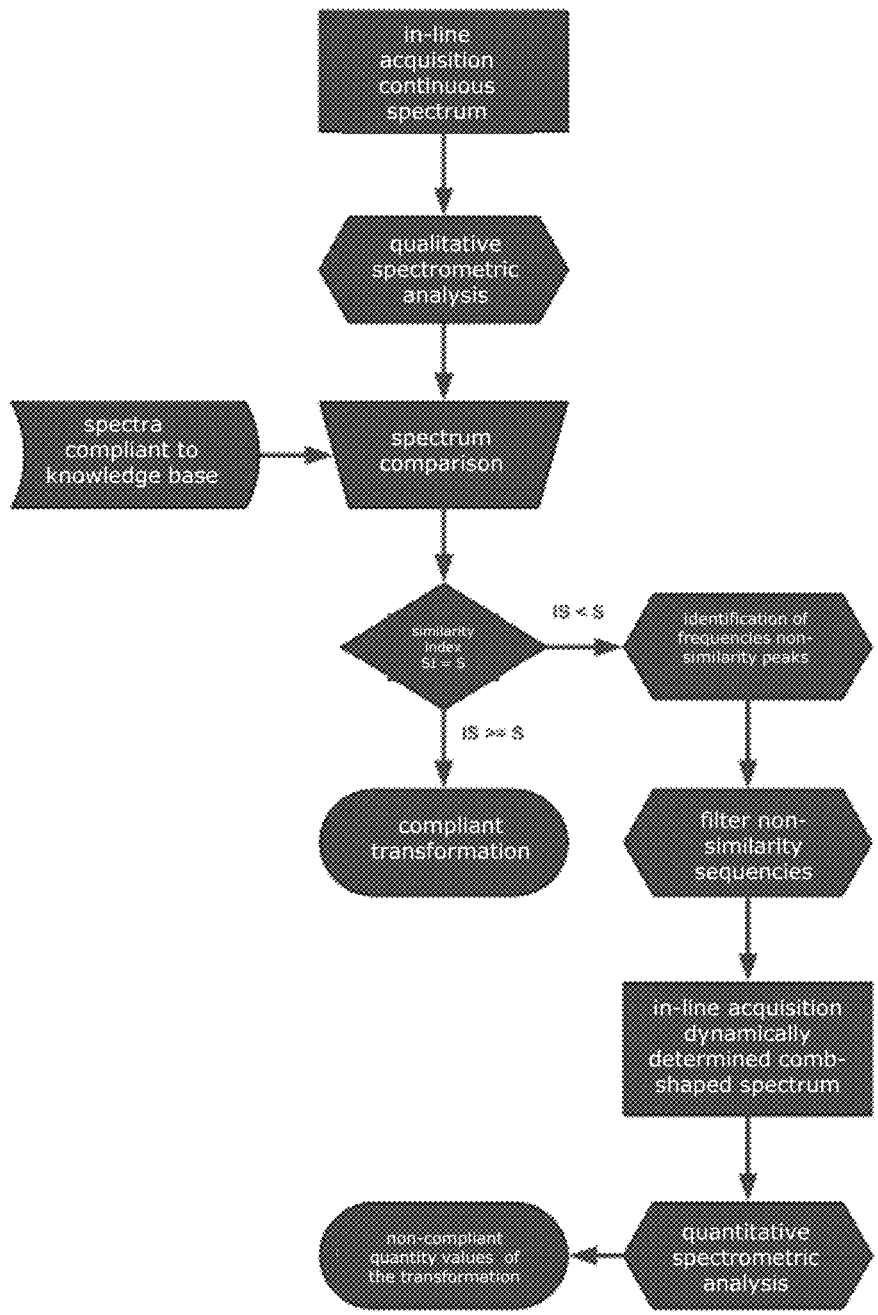
Fig. 7 – dynamic acquisition

METHOD AND ACTIVE CONTROL SYSTEM FOR FOOD TREATMENT PROCESSES

CROSS REFERENCE TO RELATED APPLICATION

This application claims priority under 35 USC 119 to Italian Patent Application No. 102020000020989 filed on Sep. 4, 2020.

BACKGROUND OF THE INVENTION

Field of the Invention

The present invention refers to a method and control system of a food process.

Background and Prior Art

As known, in the food industry sector such as the dairy, charcuterie, wine, canning industry and so on, the manufacturing processes are regulated by a number of physical/chemical parameters and by a variety of ingredients, which in the last analysis determine both the organoleptical and nutritional qualities of the finished product, and the life shelf thereof and hence commercial success.

Typically, many food products are the result of a long experimentation and derive from a traditional knowledge which has been passed on for some time and which has been refined as time went by upon changing of the environmental conditions. That implies that, except for rare exceptions, a manufacturing process in the food sector requires an extremely long time to be satisfactorily started and fine-tuned and it often does not provide a fully repeatable result, which comes at the expense of costs and of the upkeep of the quality levels appreciated by the market.

In order to face these problems, in many food industries a lot of efforts have been made to automate as far as possible the treatment processes of the raw material, so as to offer repeatable and controlled environmental conditions. That was achieved by splitting the entire manufacturing process into multiple subprocesses, each of which is carried out in an appropriate machine, which creates the suitable conditions—in terms of humidity, temperature, agitation, mechanical treatment, . . . —to perform as best as possible that individual subprocess. The raw material enters the various subprocesses, in the preset order, and is progressively processed until obtaining the final product after a time which varies according to the nature of food (for example in the dairy industry a finished product can remain within the process even various months in order to complete ripening).

However, the mechanisation and automation of the food processes is not fully satisfactory yet. That depends both on the fact that even machines require a significant fine-tuning (temperatures, speed of operation, energy employed, . . . ) in order to be able to complete the subprocess in the desired manner, and due to the very nature of the product to be treated, which is a living matter and is not always in the same expected starting conditions. This last condition often has significant effects on the outcome of the final process, because small deviations from the expected conditions at the end of a subprocess (for example in terms of acidity or of completion of fermentation or of bacterial charge or other), can translate into a shattering action downstream of the subsequent subprocesses which are started on a matter which does not exactly match expected conditions.

In the prior art it has also already been proposed to use sensors which—in addition to detecting the classic process quantities useful for automation regulation (for example temperature, flow rates, density, . . . )—provide an indication of the quality of the end product of the subprocess to act on the control. For example, WO2014103715 and WO202092648 describe food processes wherein light absorption sensors are employed to obtain information on the product.

However, even these sensors find limited use, since they provide punctual information which does not allow to regulate in a coordinated, timely and effective manner the control of the entire process. Most of all, the action which is normally performed on the manufacturing process is a classic feedback control, wherein certain upstream parameters are changed according to the data detected by the downstream sensors: this control is exhausted in the single subprocess, makes even more complex the fine-tuning and especially does not allow to optimise the entire process.

A food manufacturing plant, however automated and wisely regulated, thus requires non negligible starting times (as well as significant investments) and suffers nevertheless control and repeatability problems.

US2012/0269925 discloses a system and a method according to the preamble of the attached main claims. In particular, an automatic winemaking system is disclosed, which controls the execution of a winemaking process, by employing a number of sensors, a number of driving actuators and a database for storing winemaking data related to reference winemaking processes; optimized winemaking model is obtain through neural network training fermentation kinetics faults/alarms are signaled during the process. This arrangement, with a simple database and a neural training to get an optimized model for driving actuators, is appropriate in a simple environment like the one of grape fermentation, but doesn't prove to be satisfactory with more complex process having different sub-processes.

US2015/0299815 discloses a method for producing a desired product containing organic matter from a raw material, including the step of acquiring an absorbance spectrum of the object in which the amount of the raw material varies with progress of process. An amount or concentration of said monitored object is detected and used to establish the level which has been reached by the production process. In other words, the absorbance spectrum is used as calibrated instrument for measuring certain quantities, in turn representing certain amounts of monitored object, on which to investigate.

US2015/0366219 discloses a monitoring process and system for heating treatment of food. WO2010/025254 discloses a system for measuring acrylamide in food products, by detecting wavelength emission data from food.

The need is hence felt to provide a control system of complex industrial food processes based on a plurality of different sub-processes, which solves the above-mentioned problems, without the need to change the arrangement of usual equipment and of the automations currently employed in food industries.

SUMMARY OF THE INVENTION

The object of the present invention is therefore to provide a control method and system for food processes which can be applied to existing manufacturing plants and provide timely and automatic regulation controls, preferably exploiting synergies between various optimised parallel processes.

A solution according to the invention is achieved by means of a control method and system having the features defined in the independent claim herewith attached. Other preferred features of the invention are defined in the dependent claims.

In particular, according to a first aspect of the invention, it is provided a control system of a food treating process made of a plurality of sub-processes, comprising
- a plurality of product sensors, apt to detect characteristic sensor data of a food material being processed in each single subprocess,
- a plurality of plant sensors, apt to detect sensor data relating to operating quantities of single treatment machines which control each of said subprocesses,
- a plurality of control devices, apt to adjust process parameters of said treatment machines,
- a main hardware and software architecture apt to process said characteristic sensor data of food material depending on said sensor data of operating quantities of treatment machines for a plurality of subprocesses making up in sequence said treatment process,
- a database structure, wherein all said sensor data of food material and operating quantities for said plurality of subprocesses are stored for a plurality of treatment processes, wherein
- said main hardware and software architecture comprises a machine learning module which defines a driving metric of said subprocess control devices based on said characteristic sensor data of food material in a plurality of subprocesses making up in sequence a treatment process,
- said product sensors comprise at least
- a spectrograph apt to acquire spectrographic spectrum of a food material being processed in a subprocess, and
- a thermograph apt to acquire thermographic spectrum of food material in said same subprocess,
- said spectrographic spectrum and thermographic spectrum being processed in said main hardware and software architecture in a way correlated and combined in time, and wherein
- said driving metric of said subprocess control devices is defined based on a comparison of a current spectrographic spectrum and current thermographic spectrum with a reference spectrographic spectrum and reference thermographic spectrum.

According to another aspect, at least said spectrographic spectrum is a frequency spectrum which is analysed for detecting the presence of deviation of quantities with respect to a reference frequency spectrum for the respective subprocess stored in said database.

Said spectrograph sensor is preferably an NIR-MIR sensor, which acquires transmittance/reflectance spectra.

Preferably, said thermographic spectrum is acquired with image sensors in the infrared range.

Further, said hardware and software main architecture includes at least a processing unit (CPU) and a relative data memory.

Preferably, said machine learning module is configured with a predictive analysis engine and a proactive analysis engine.

According to another aspect of the invention, it is provided a control method of a food treatment process which uses a system as in any one of the preceding claims, wherein the following steps are performed:
- adjusting process parameters of a plurality of treatment machines by means of control devices, along a plurality of food treatment subprocesses,
- in said plurality of food treatment subprocesses acquiring product characteristic sensor data by means of product sensors and acquiring sensor data relating to operating quantities by means of plant sensors, said product sensors comprising at least a spectrograph apt to acquire spectrographic spectrum of a food material being processed in one of said subprocesses, wherein
- said product characteristic sensor data are processed by means of said hardware and software main architecture based on said sensor data relating to operating quantities for a plurality of subprocesses making up in sequence said treatment process,
- storing said product characteristic sensor data and sensor data relating to operating quantities in a database structure, for a plurality of treatment processes, associating said characteristic sensor data and sensor data relating to operating quantities with a grade flag which represent a qualitative assessment of a corresponding food product downstream of said subprocesses,
- said hardware and software main architecture comprising a machine learning module which determines and output drive data for subprocess control devices of a current subprocess based on product characteristic sensor data detected in said current subprocess and based on said characteristic sensor data, sensor data relating to operating quantities and flags stored in said database structure.

Preferably, said step where said machine learning module determines drive data, provides a comparison between spectrographic spectrum of said current subprocess with respect to a reference spectrographic spectrum stored in said database, identifying a deviation used as new input in said machine learning module.

BRIEF DESCRIPTION OF THE DRAWINGS

Further features and advantages of the invention will in any case be more evident from the following detailed description of preferred embodiments of the same, provided as a non-limiting example and illustrated in the attached drawings, wherein:

FIG. 6 is a functional diagram of a preferred embodiment of the invention.

FIG. 7 shows a flow diagram exemplifying the dynamic acquisition of non-complying quantities.

DETAILED DESCRIPTION OF PREFERRED EMBODIMENTS

A process control system is implemented in a production, transformation and distribution chain of a food product, which extends for example from the acquisition of the raw material (ingredients) to the storing of the finished product on a shelf (at the point of sale).

The process is split into multiple steps or subprocesses, according to operating criteria connected to the specific machine or treatment carried out on the product being processed. For example, a subprocess in the dairy industry can be milk pasteurisation, since such processing occurs within an individual machine before moving to the next step of process. Similarly, an exemplifying subprocess in the oil industry is olive pressing and in the wine industry is tumultuous fermentation.

Figure 1:
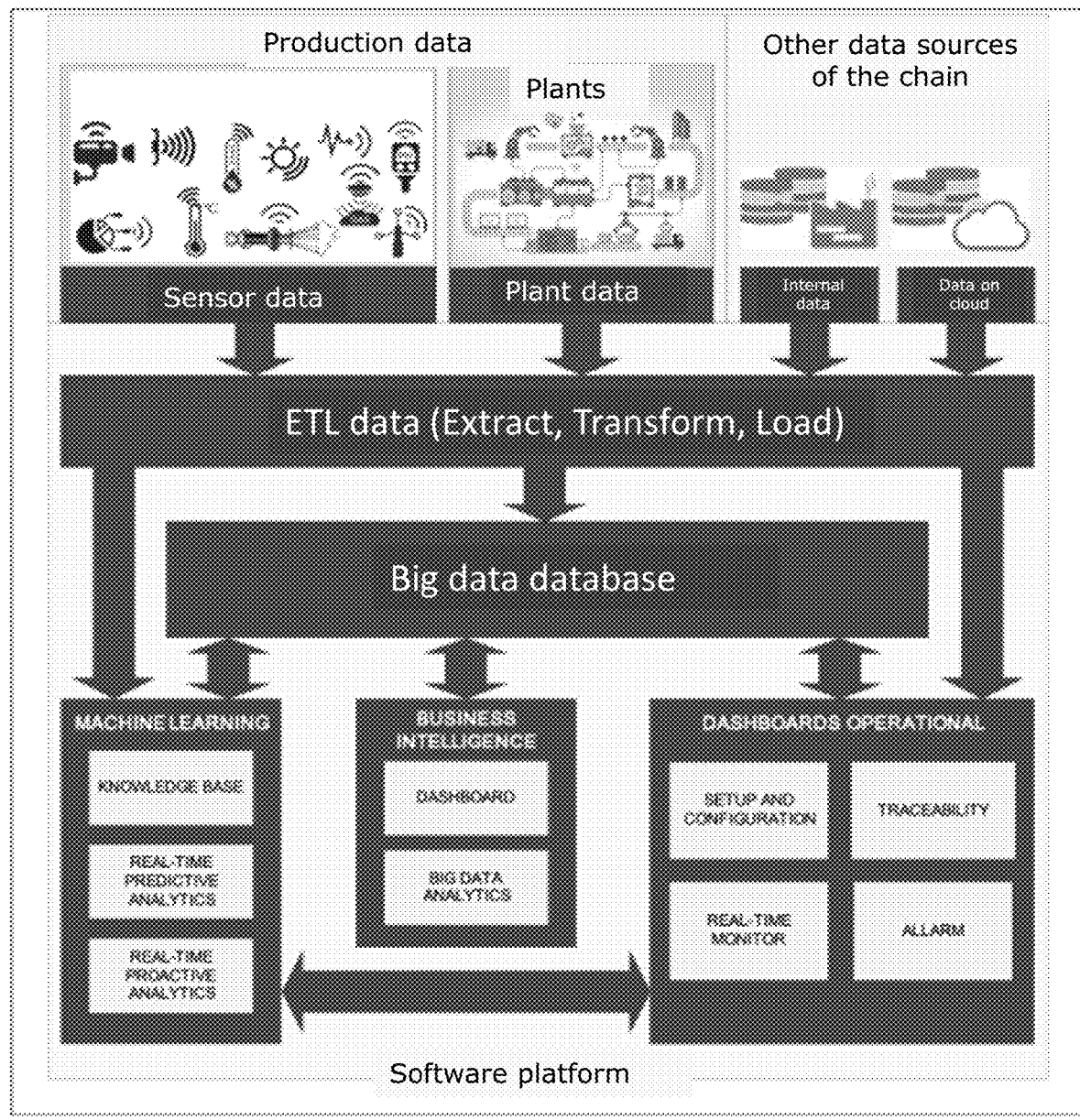
FIG. 1 is a schematic flow diagram which illustrates the architecture of the system according to the invention.
Figure 2:
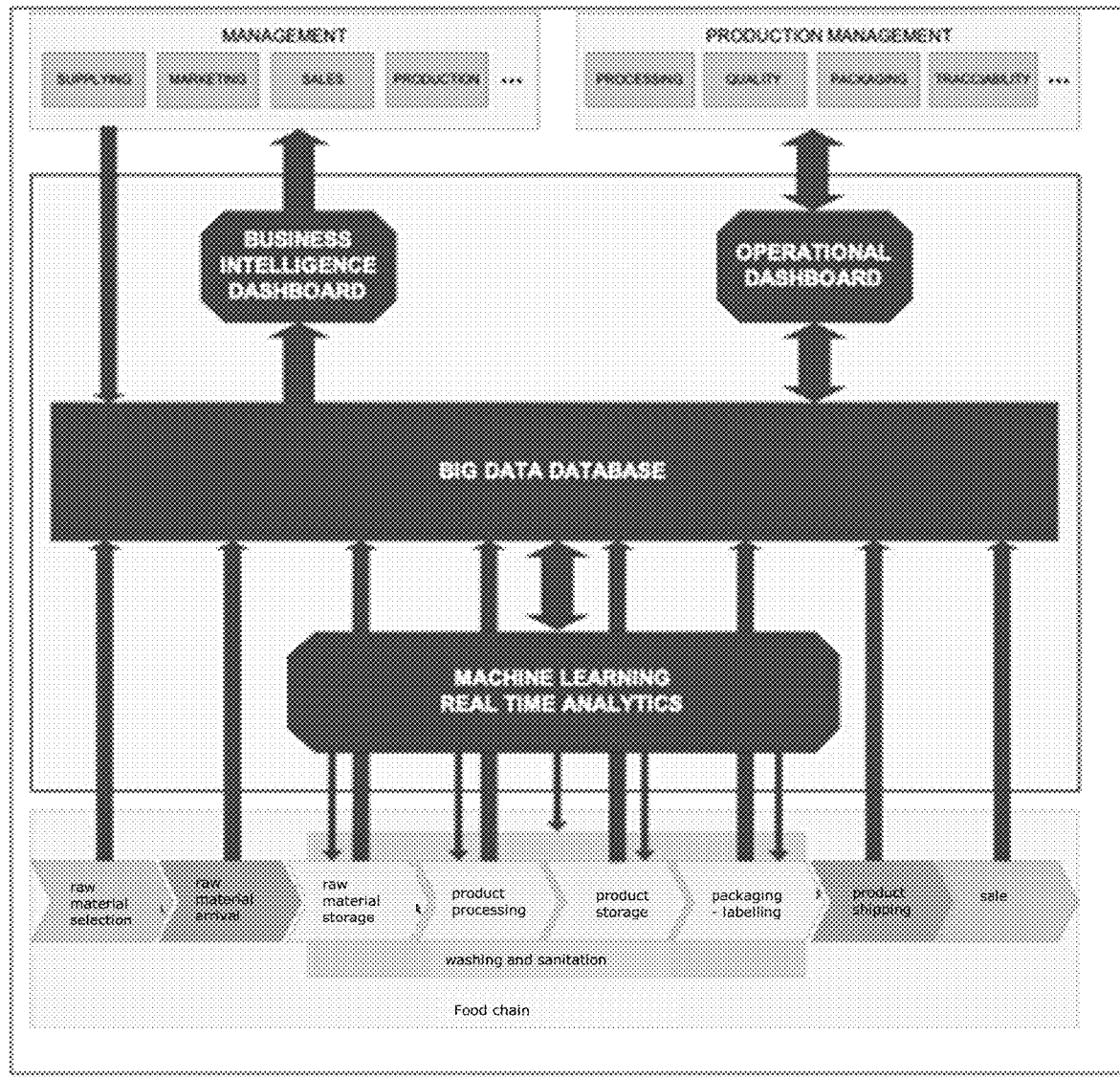
FIG. 2 is a flow diagram which illustrates a logical diagram of the system according to the invention.

In the control system (FIG. 1) there are provided at least
- a plurality of product sensors, which detect composition features of the product in the individual subprocess, the product being possibly different from subprocess to subprocess,
- a plurality of plant sensors, which detect the operating quantities (pressure, temperatures, flow rates, . . . ) of the individual machines accommodated in the treatment plant which regulate the manufacturing process,
- a plurality of control devices, by which to regulate the process parameters (temperature, times, flow rates, . . . ) defined by the plant,
- a "core hardware and software" architecture, wherein data coming from the sensors are processed,
- a data base or "big data" structure, wherein all the data of multiple production subprocesses are stored.

Product sensors acquire specific quantities of the product being processed within a subprocess. For example, physical quantities are acquired such as temperature, density, pressure, relative humidity, but also chemical quantities such as acidity, concentrations of ingredients and other. In particular, according to the invention, by means of a spectrograph, a spectrographic analysis of the product is carried out and the spectrographic data thereof are acquired as a sort of 'signature' or 'track' of that monitored product in that specific work condition.

The control devices are classic actuators, such as valves, thermostats, injectors, agitators, . . . which affect the physical operation parameters of the plant, in particular of each subprocess.

The "hardware/software core" architecture comprises at least a processing unit (CPU) and a data memory thereof, through which a processing software of the data coming from the sensors and from the "big data" structure is made to run.

In particular, the hardware/software core comprises a machine learning module configured with a predictive analysis engine and a proactive analysis engine, suitable for processing the incoming sensor data and for determining outgoing regulation parameters to be used for driving said control devices.

The control system according to the invention hence consists of (a) a main architecture, consisting of the Big Data structure and of the machine learning modules (including Artificial Intelligence modules and Business Intelligence modules), (b) an evolutive hardware/software platform, which develops and evolves according to the incremental results acquired by the main architecture and based on the sensors employed (which are made according to a continuously developing technology) and (c) a plant for the treatment of food matter equipped with the relative process machines (boilers, mixers, coolers, reactors, extruders, . . . ).

In the main architecture (a) sensor data received from the sensors are stored in the Big Data structure (content repository), which are subsequently analysed to extract useful information for driving the control devices which, in turn, affect the new data acquired by the sensors in the process machines of the plant, in a continuous learning cycle which is not carried out only on a single subprocess, but on the data obtained from the entire process chain made by the sum of the various sub-processes.

Figure 5:
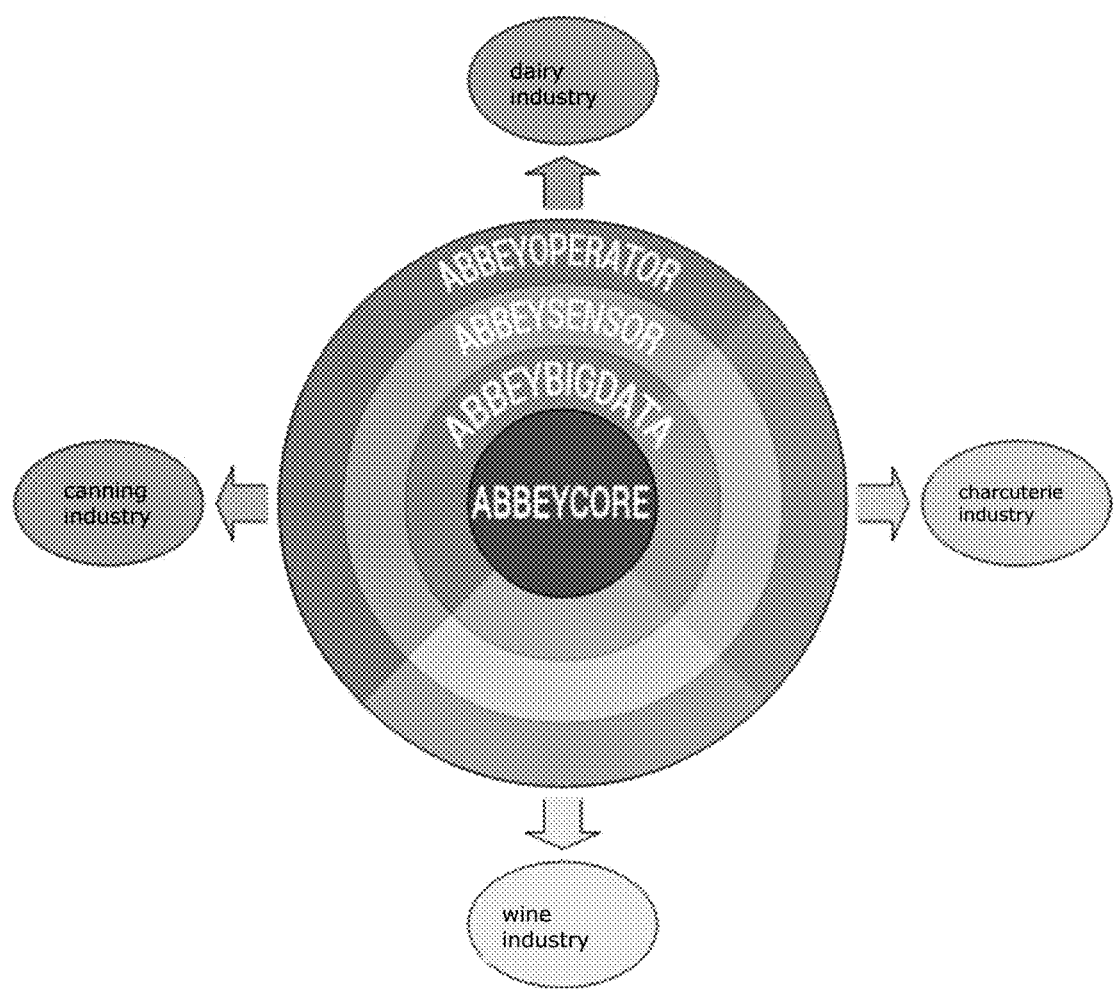
FIG. 5 is a diagram of the potential interactions of the control system according to the invention with various industrial food sectors.

In the main architecture (a) a data base made with the Big Data structure representative of the transformations of the raw material into intermediate products and then a finished product in the specific process is hence processed and stored. Said data base is built with sensor data of a specific process, but it can be fetched with sensor data coming from multiple parallel processes belonging to different food industries (see FIG. 5).

In the hardware/software platform (b) the processing of the sensor data occurs which are continuously and automatically received from the sensors.

The specific plant (c) applies the results of the processing of the above-said platform (b), through the relative control devices, in the specific production context of the food industry which implements the control system of the invention, in order to obtain a correct transformation of the raw material and intermediate products, both to obtain the product with the desired organoleptic features, and to avoid the occurrence of failures or product alterations which might also occur in an untimely way during the distribution or on-shelf exhibition step.

Once the control system is deployed at a desired transformation plant, an array of product sensors and plant sensors send the collected sensor data, relating to the physical, chemical, microbiological quantities which govern the transformation of the raw material and intermediate products, to the "core hardware/software" architecture. In this core architecture, a machine learning module, through suitably selected predictive and proactive artificial intelligence metrics, processes the collected sensor data and, based on the final outcomes of the subprocesses (in particular defined on the basis of the deviation between the spectrographic analysis of a current product and of a product considered 'optimal') 'learns' to distinguish the quantities which lead to a perfect product from those which lead to a spoiled product. The control system hence detects and signals (for example with a sound or light warning on an alert device of the subprocess) the anomalies detected on the quantities of the specific subprocess.

As a result of these sensor data acquisitions and processing from the sensors, a data base is built relating to the transformations of the raw material in the food industry on multiple parallel processes (FIG. 5), for example in the dairy, charcuterie, wine, canning industry. As a matter of fact, the data base contains consistent data, because they come from sensors of similar technology, which can hence reside on the same platform where the same machine learning module operates.

Operatively, the operation of the control system provides the following actions.

The system stores all the sensor data which automatically come in real time from the sensors located on various sensing stations from the beginning to the end of the transformation process of the raw material into the finished product. The sensors collect continuously and along the entire path wherein food material is daily transformed, all the sensor data coming from the physical, chemical, microbiological subprocesses, preferably including the sensor data relating to the food material features even during and after distribution, in correspondence of final products then considered satisfactory or non satisfactory.

Once all these sensor data have been collected in correspondence of the exact moment of the process in which the transformations occurred, the control system is capable of building a data base wherein the values of the quantities are identified, including the spectrographic analyses, which have led to a satisfactory product and, conversely, it is capable of determining the event or multiple events which have led to a spoiled or altered product or in any case a non satisfactory product.

By machine learning analysis, the control system is capable of interpolating and identifying other intermediate drift conditions—based on further data detected by the sensors—which are considered having a drift from the design condition. Upon detecting these draft conditions, a correction can be implemented by timely driving the control devices of the process. Alternatively, if detected drift conditions are considered source of strong anomalies, they are signalled by the alert devices.

By repeating multiple times these operations, the control system suitably updates its data base relating to the transformation processes, allowing to perform analyses based on standard techniques such as OLAP technique as well as on advanced artificial intelligence techniques. In particular, the machine learning metrics are used for refining the predictive ability of the system even in situations of detected data unusually different from the predictable ones.

The control system is hence capable of guiding the transformation processes of the raw material and intermediate products, the state transitions and the dynamic transformations thereof, both fast ones (for example curd in the case of cheese), and slow ones (such as salting of cured meats) up until very slow ones (such as ripening).

Preferably, the control system acquires the sensor data at an entry step of the raw material in the process, determining the starting condition in which the raw material is found when transformation thereof has not begun yet, so as to prepare the treatment parameters of the process in a work condition suitable for the best use of the specific starting raw material. For example, the process could start from the very beginning a more prolonged pasteurisation step—hence with temperature rise and descent ramps different from a standard pasteurisation—should an abnormal micro bacterial charge be detected in the raw material (raw milk) at entry, instead of correcting the pasteurisation treatment if abnormal values were detected downstream the subprocess. The same control system, in the presence of abnormal micro bacterial charge on the raw material can act even more upstream in the process chain, if sensor data of the environmental conditions (for example hygiene parameters or extraction methodology of the raw material) and on the feeding (for example spectrographic features of the food) of the animals which have generated that raw material is available.

In short, the control system according to the invention does not simply cooperate with the digitalisation and automation of the transformation process on the basis of a "recipe", rather it acts on the process parameters for controlling and guiding the development thereof on the basis of the analyses of the sensor data sampled by the sensors and by the results of a processing with AI algorithms trained with the data base built on the entire processes carried out in parallel.

In essence, the control method of the food treatment process provides at least to
  regulate process parameters of a plurality of treatment machines by driving control devices, along a plurality of food treatment subprocesses,
  in a plurality of the food treatment subprocesses, acquiring sensor data characteristic of the raw material and intermediate product through product sensors and acquiring sensor data relating to the operating quantities through plant sensors.

In an original way, the sensor data characteristic of the raw material and intermediate products are processed through a hardware/software main architecture depending on the sensor data relating to operating quantities for a plurality of subprocesses making up in sequence the treatment process. Then, the sensor data characteristic of the product and the sensor data relating to operation quantities are stored in a data base structure, for a plurality of treatment processes, associating these sensor data with a grade which results from a quality assessment (a ranking based on the fact that the products are considered acceptable or non acceptable, according to a scale of values, for example two, three, four or five or more) of corresponding final products downstream of the processes. In the hardware/software main architecture a machine learning module is included which perform a determination step where driving parameters are determined for the control devices of a current subprocess on the basis of sensor data characteristic of the product detected in the current subprocess and of the sensor data and grade detected previously and stored in the data base structure.

In the determination step performed by the machine learning module a comparison is provided at least between spectrographic data of the current subprocess with respect to the spectrographic data of the data base, identifying a deviation which is used as new input in the machine learning module.

At framework level, the control system is preferably built using an approach with 'microservices', that is the software architecture is characterised by small applications capable of performing elementary functions (including the alert generators and the trend predictors of the transformation process), which can be easily used in the system without the need to resort to burdensome 'rebooting' of the entire system. The interaction between 'microservices' is managed through suitable tools (software/hardware) for coordination and orchestration (orchestrator).

With specific reference to predictive and proactive activities, it has been detected that it is preferable to build the hardware/software architecture by resorting to neural networks (even in their most recent declination, called 'Deep Learning'). The preference for neural networks is due in particular to their versatility in managing different types of data, as well as to the ability of carrying out 'feature extraction' activities in a fully natural manner.

Moreover, unlike the prior art, which provides to use sensors for sampling always the same type of quantities (and in the same ways) in the same process locations, according to the invention also data acquisition is performed in a dynamic manner. As a matter of fact, since also the transformation process has dynamic behaviour and results—which precisely explain why there is a deviation between the sensor data acquired by the sensors and those which should be had if the process followed an ideal trend—it is suitable to consider also data acquisition activities as a dynamic process.

Accordingly, sensor data are dynamically acquired by product sensors and plant sensors, depending on the evolution of the data base built by the system during operation.

The active control described here is a dynamic control since, according to an original feature thereof, it is guided by the consistent comparison between spectroscopic data sets that do not require the knowledge of specific biochemical quantities to be monitored, whose purpose is precisely to identify, dynamically, the quantities which determine a non-consistence between the spectra acquired in real time and reference spectra.

The dynamic data acquisition and the dynamic control of the transformation of raw food material into a finished product ready for consumption constitute a preferred feature of the invention.

A. The method can run without predetermined constraints on the quantities to be monitored, as the quantities to be investigated and put under observation derive from the comparison of the spectra from which the non-consistence quantities can raise up.

B. The consequence of the aforementioned undefinition of the quantities to be controlled does not put limits on the discovery of new scientific knowledge that is currently impossible to be identified under the methodologies in use today.

C. The variables acquired and to be investigated can therefore be potentially infinite.

D. Since the number of transformation processes that are investigated, acquired, analyzed and 'learned' (Big Data-Data Analysis-Machine Learning) through the spectra comparison is potentially infinite, the perfection of the predictive and proactive system is also tending to infinity.

Therefore, with the system of the invention, the transformations are no longer guided by the monitoring of a certain set of physical/biochemical quantities, predefined a priori on the basis of a fixed recipe, which do not take into account the dynamic variation of the characteristics of the raw/intermediate food material, of the environmental conditions and plants.

The peculiarity of this model is instead that of making possible the dynamic identification of physical/biochemical quantities which in an unpredictable but decisive way can influence the transformation phase and which in theory, in that specific phase, should instead could have been irrelevant should they not be among the monitored quantities.

These data also enrich the knowledge base with information that is not theoretically computed and therefore assume fundamental importance also in the automatic learning of the "intelligent" portion of the system, to improve its capabilities and performance over time.

The dynamic identification of these quantities therefore affects the predictive analysis which can thus be much closer to reality and consequently the analysis becomes more precise to determine the proactive actions aimed at correctly guiding the transformation process.

FIG. 7 shows a flow diagram exemplifying the dynamic acquisition of non-complying quantities.

Figure 3:
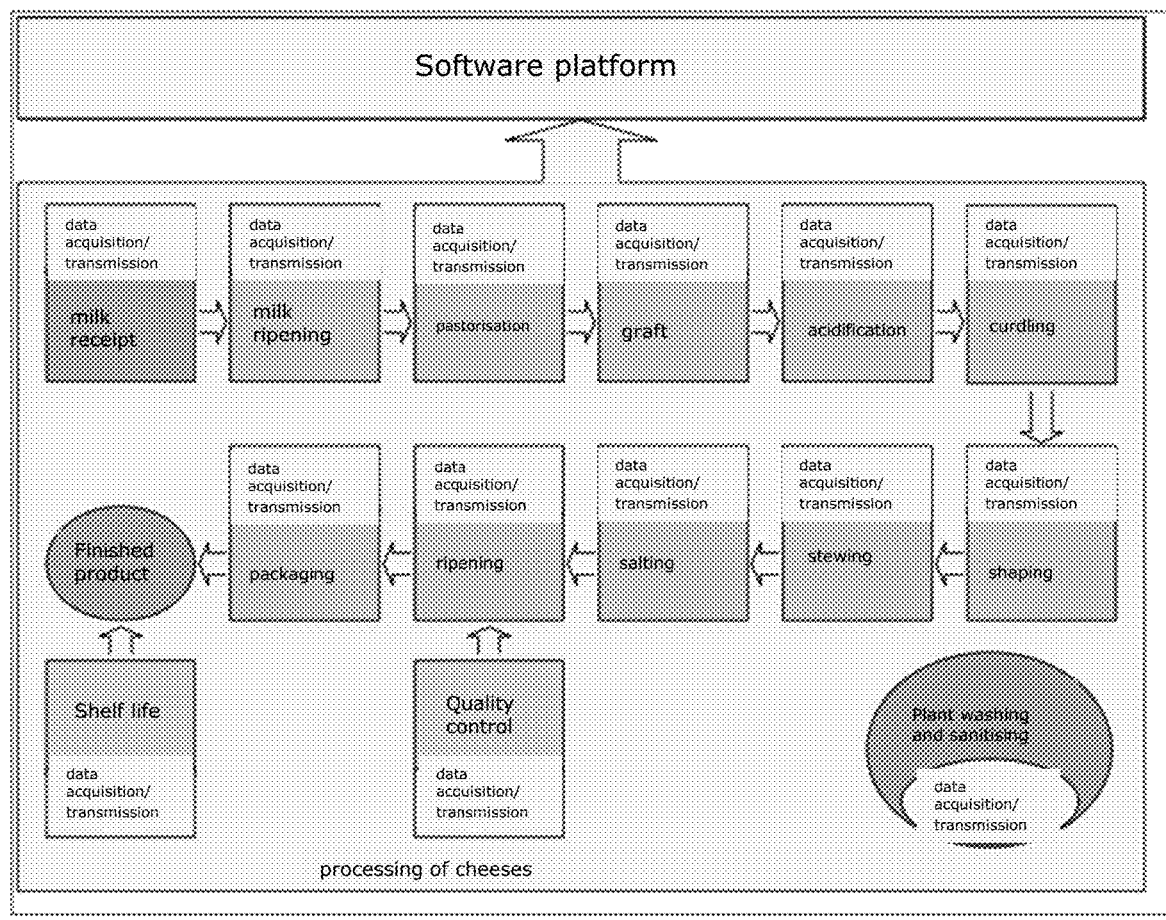
FIG. 3 is a logical diagram which illustrates a possible example of the control system applied to the dairy industry.
Figure 4:
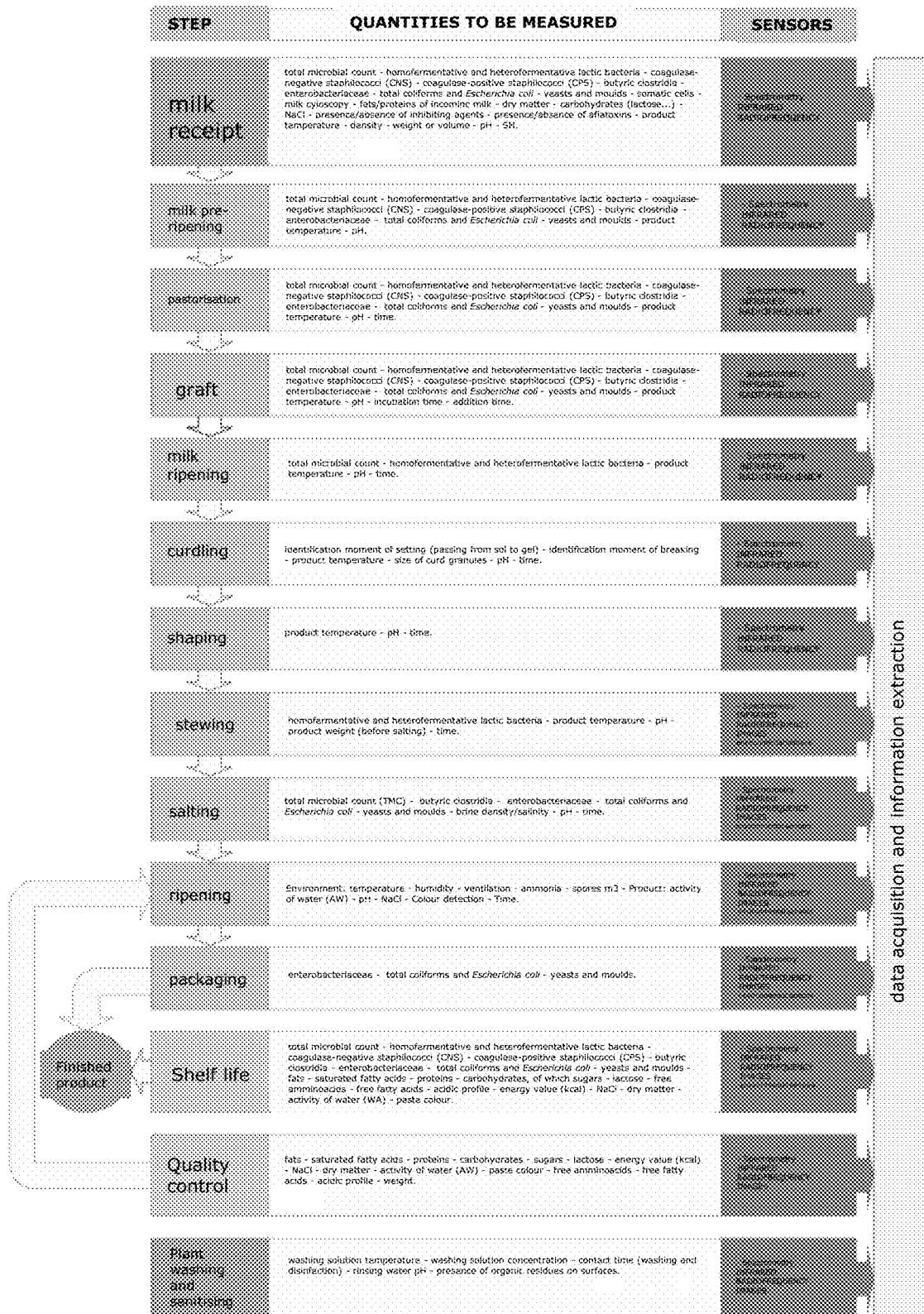
FIG. 4 is an exemplifying table of the sensors and of the quantities detected in the various subprocesses in the case illustrated in FIG. 3.

FIGS. 3 and 4 illustrate schematically some steps provided by the control system according to the invention, applied to a treatment process in the dairy sector.

As it can be detected from the diagrams reported in the drawings, in each treatment step or subprocess, by means of product sensors and plant sensors the acquisition of sensor data relating to quantities relevant for the subprocess is provided. In particular, it must be noted that for each subprocess step the spectrometric analysis of the raw material or intermediate product being processed is performed.

As a matter of fact, according to a peculiar feature of the invention, the control system provides at least a product sensor consisting of a spectrograph.

In particular, a NIR-MIR sensor is used for monitoring the raw material or intermediate product being transformed and obtaining thus a series of sensor data, which, suitably analysed, allow to characterise in detail the intermediate product being transformed in the specific subprocess to which the NIR-MIR spectrographic sensor belongs.

According to the invention, the spectrum in frequency of the NIR-MIR sensors is not traditionally used as calibrated instrument for measuring certain quantities on which to investigate, but for detecting the presence of abnormal quantities, with respect to a reference spectrography of that product in that subprocess step, which are an index of a deviation from the expected transformation subprocess. The deviation from the desired subprocess is therefore detected by the spectroscopic analysis not of specific monitored quantities, of the transformation being carried out in its completeness in that specific step (for example in a curd step).

The control system, due to the data base gathered in time, performs a quality comparison between spectroscopy (spectrographic data) of that transformation step being carried out in that specific subprocess, with respect to the expected one: if the two spectroscopies do not coincide, a deviation or anomaly is determined which is used as a new incoming piece of data in the AI processing module, so as to obtain output drive data for the suitable control device(s), which is calibrated depending on the control metrics processed for the entirety of the process.

According to a further preferred variant, such spectrographic analysis is employed in a correlated manner combined with a thermographic analysis synchronised in time on the same subprocess. Such combined analysis allows the continuous monitoring of the transformations of the raw material or intermediate product being carried out in the specific subprocess in a fully novel manner. As a matter of fact, this way a combined information is obtained on the dynamic of the transformations of the raw material in a complete manner and not only on one or more particular quantities to be investigated upon. The comparison of this combined information with the corresponding information stored in the data base of the system, exploiting the Machine Learning modules, highlights either the full match or the mismatch between the two pieces of information, thus allowing in progression to make fully reliable predictive analyses and, following which, to carry out effective proactive actions in order to obtain a process control which easily converges towards a food product of excellence.

FIG. 6 illustrates schematically this peculiar feature of the system.

Within the individual subprocesses, the raw material or intermediate product (collectively referred to as 'food material') being processed is analysed with product sensors of various technology, in particular:

1. Near infrared and medium infrared sensors (NIR-MIR), by which transmittance/reflectance spectra are acquired (depending on the step) to obtain biochemical information on the food material (spectroscopy);
2. Image sensors (IR), by which images in the infrared spectrum are acquired in order to obtain diffused information on the temperature of the food material (thermography);
3. Chemical-physical sensors, by which specific quantities of both the food material and the environmental parameters (temperature, humidity, gas, ventilation, etc.) are measured.

The provided data acquisitions are hence relative to (i) the features of the raw material upon arrival and then, (ii) for each transformation step:
a. features of the food material at the beginning of the transformation step Ni;

b. Time, spectroscopic and thermographic sampling of the transformation step Ni;

c. Detection of the trigger time and of the duration of any condition transitions during the transformation step Ni;

d. Time sampling of the environmental parameters (temperature, humidity, gas, ventilation, etc.) which can affect the transformation step Ni;

e. Features of the food material at the end of the transformation step Ni.

Finally, data relating (iii) to a final quality control are also acquired:

a. table of the organoleptic features of the finished product;

b. Shelf-life for the packaged product.

The assembly of all these concatenated data, which range from the raw material to the organoleptic features of the finished product, makes up the digital identity card of the manufacturing process of the specific product and are stored in the system data base.

The integration of the information obtained in all these steps allows to obtain output drive data (meant for the control devices of the individual subprocesses) which correlate all the aspects of the entire manufacturing process.

This monitoring model of the manufacturing process also allows to obtain further analyses which make the predictive behaviour more effective, in particular:

1. a correlation analysis of the spectra and of the spectrum transitions (both of the spectra in frequency and of the heat maps) of the product being processed with the data of the environmental quantities (should they affect the transformation step);

2. a correlation analysis between the spectrographic data (spectroscopy) and the thermographic data, with further comparison against the data of the data base;

3. direct comparison of the spectra and of the spectrum transitions (both of the spectra in frequency and of the heat maps) against the data of the data base;

4. a quantitative analysis of the current spectra should they have a Similarity Index (IS)—intended as the inverted number of the difference between current spectrography and the design spectrography previously acquired on an optimal product and stored in the data base—below a certain threshold (IS=1 completely different spectra, IS=∞ identical spectra).

With the control mode of the system of the invention it is possible to quickly act on the evolution of the industrial manufacturing process, even without being able to have an action by a human operator who, according to the known art, based on his/her experience was capable of quickly correcting any process anomalies through continuous observation.

The peculiarity of the system of the invention lies precisely in its ability to analyse the product being processed in real time, using sensors apt to transfer data peculiar of a subprocess to a predictive module trained with machine learning techniques on the data present in the entire transformation process which is part of the production chain.

The system of the invention, with respect the conventional approach which just provides for monitoring of a certain assembly of quantities established beforehand, allows to detect biochemical quantities which in an unexpected manner can affect in a decisive way the transformation step and which in theory, in that specific step, should have been irrelevant, so that they would not have fallen among the quantities to be monitored. These data enrich the data base with information not calculated theoretically, therefore they contribute in a non-marginal way to the automatic learning of the system and to the building of the operation metrics of the machine learning software. This has an impact on the predictive analysis, which can thus be much more adhering to reality and consequently the analysis for determining the proactive actions aimed at correctly driving the control devices and hence the production process becomes more precise.

Advantageously, the control system of the invention also allows to run backwards the concatenation of the process data on the various subprocesses, so as to identify for example any biochemical quantities which could act as warning biomarkers of the onset of degenerative processes or, vice versa, of virtuous ones. Once this knowledge has been acquired in the data base, the same biomarkers can be detected by suitable sensors and be regularly used for the prediction process of the control software.

As can be seen from the above reported description, the control system according to the invention allows to perfectly achieve the objects set forth in the premises. As a matter of fact, the provision of a series of product sensors and of a hardware/software infrastructure where the processing architecture and machine learning architecture is hosted as well as of the data base, allows to obtain an optimal control of the entire transformation process of the food product. The system takes into account a number of indexes which act on the entire process, including the condition of the incoming raw material and the behaviour of the product in the distribution and on-shelf-display subprocess.

Finally, due to the use of a scalable data base enriched with data detected on multiple processes in parallel, it is possible to offer a control system usable both on a single industrial activity, and synergistically on multiple similar industrial activities as well as on industrial activities in different food sectors.

However, it is understood that the invention must not be considered limited to the particular illustrated configurations and examples, which must be considered non-limiting of the scope of the invention, but that different variants are possible, all within the reach of a person skilled in the field, without departing from the scope of protection of the invention, which is only defined by the following claims.

What is claimed is:

1. A control system of a food treating process made of a plurality of sub-processes, comprising a plurality of product sensors, apt to detect characteristic sensor data of a food material being processed in each single subprocess, a plurality of plant sensors, apt to detect sensor data relating to operating quantities of single treatment machines which control each of said subprocesses, a plurality of control devices, apt to adjust process parameters of said treatment machines, a main hardware and software architecture apt to process said characteristic sensor data of food material depending on said sensor data of operating quantities of treatment machines for a plurality of subprocesses making up in sequence said treatment process, a database structure, wherein all said sensor data of food material and operating quantities for said plurality of subprocesses are stored for a plurality of treatment processes, characterized in that said main hardware and software architecture comprises a machine learning module which defines a driving metric of said subprocess control devices based on said characteristic sensor data of food material in a plurality of subprocesses making up in sequence a treatment process, in that said product sensors comprise at least
a spectrograph apt to acquire spectrographic spectrum of a food material being processed in a subprocess, and
a thermograph apt to acquire thermographic spectrum of food material in said same subprocess,
said spectrographic spectrum and thermographic spectrum being processed in said main hardware and software architecture in a way correlated and combined in time, and in that
said driving metric of said subprocess control devices is defined based on a comparison of a current spectrographic spectrum and current thermographic spectrum with a reference spectrographic spectrum and reference thermographic spectrum.

2. The control system as in claim 1, wherein at least said spectrographic spectrum is a frequency spectrum which is analysed for detecting the presence of deviation of quantities with respect to a frequency spectrum of a reference spectrum for the respective subprocess stored in said database.

3. The control system as in claim 1, wherein said spectrograph is an NIR-MIR sensor.

4. The control system as in claim 3, wherein said NIR-MIR sensor acquires transmittance/reflectance spectra.

5. The control system as in claim 3, wherein said thermographic spectrum is acquired with image sensors in the infrared range.

6. The control system as in claim 1, wherein said hardware and software main architecture includes at least a processing unit (CPU) and a relative data memory.

7. The control system as in claim 6, wherein said hardware and software main architecture is built as a neural network.

8. The control system as in claim 1, wherein said machine learning module is configured with a predictive analysis engine and a proactive analysis engine.

9. A control method of a food treatment process which uses a system as in claim 1, wherein the following steps are performed:

adjusting process parameters of a plurality of treatment machines by means of control devices, along a plurality of food treatment subprocesses,
in said plurality of food treatment subprocesses acquiring product characteristic sensor data by means of product sensors and acquiring sensor data relating to operating quantities by means of plant sensors, said product sensors comprising at least a spectrograph apt to acquire spectrographic spectrum of a food material being processed in one of said subprocesses, characterised in that
said product characteristic sensor data are processed by means of said hardware and software main architecture based on said sensor data relating to operating quantities for a plurality of subprocesses making up in sequence said treatment process,
storing said product characteristic sensor data and sensor data relating to operating quantities in a database structure, for a plurality of treatment processes, associating said characteristic sensor data and sensor data relating to operating quantities with a grade flag which represent a qualitative assessment of a corresponding food product downstream of said subprocesses,
said hardware and software main architecture comprising a machine learning module which determines and output drive data for subprocess control devices of a current subprocess based on product characteristic sensor data detected in said current subprocess and based on said characteristic sensor data, sensor data relating to operating quantities and flags stored in said database structure.

10. The method as in claim 9, wherein said step where said machine learning module determines drive data, provides a comparison between spectrographic spectrum of said current subprocess with respect to a reference spectrographic spectrum stored in said database, identifying a deviation used as new input in said machine learning module.

* * * * *